United States Patent [19]
Felder et al.

[11] Patent Number: 5,668,010
[45] Date of Patent: *Sep. 16, 1997

[54] METHOD FOR DETERMINING THE ANTIMICROBIAL AGENT SENSITIVITY OF A NONPARAFFINOPHILIC MICROORGANISM USING VARIOUS MILIEUS AND AN ASSOCIATED APPARATUS

[75] Inventors: Mitchell S. Felder, Hermitage; Robert A. Ollar, Milford, both of Pa.

[73] Assignee: Infectech, Inc., Sharon, Pa.

[ * ] Notice: The term of this patent shall not extend beyond the expiration date of Pat. No. 5,316,918.

[21] Appl. No.: 620,092

[22] Filed: Mar. 21, 1996

Related U.S. Application Data

[62] Division of Ser. No. 556,033, Nov. 9, 1995, Pat. No. 5,641,645.

[51] Int. Cl.$^6$ .................................................. C12M 3/00
[52] U.S. Cl. .................... 435/287.9; 435/288.1; 435/288.3; 435/810; 435/975
[58] Field of Search ................ 435/287.9, 288.1, 435/288.3, 810, 975

[56] References Cited

U.S. PATENT DOCUMENTS

| | | | |
|---|---|---|---|
| 2,784,146 | 3/1957 | Goldman | 435/288.1 |
| 3,826,717 | 7/1974 | Gilbert et al. | 435/288.4 |
| 3,966,552 | 6/1976 | Pagano et al. | 435/288.1 |
| 4,683,195 | 7/1987 | Mullis et al. | 435/6 |
| 4,683,201 | 7/1987 | Hamill et al. | 435/75 |
| 4,683,202 | 7/1987 | Mullis | 435/91 |
| 5,153,119 | 10/1992 | Ollar | 435/34 |
| 5,316,918 | 5/1994 | Ollar | 435/34 |

FOREIGN PATENT DOCUMENTS

| 1129324 | 8/1982 | Canada | C12Q 1/02 |
|---|---|---|---|

OTHER PUBLICATIONS

Wallace et al., *Chest*, 93, (5) 926–932 (1988).
Wolinsky, *American Review of Respiratory Disease*, vol. 119: 107–159 (1979).
Horsburgh, Jr. et al., *Medicine*, vol. 64, No. 1: 36–38 (1983).
Horsburgh, Jr. et al., *American Review of Respiratory Disease*, 139: 4–7 (1989).
C.M. Reichert et al., *Aids: Etiology, Diagnosis, Treatment and Prevention*, p. 134, Lippencott (1985).
C.C. Hawkins et al., *Annals of Internal Medicine*, 105: pp. 184–188 (1986).
J. Hoy et al, *The Journal of Infectious Diseases*, 161: 801–805 (1990).
Fuhs, G.W., *Arch Mikrobiol*, 39: 374–422 (1961).
Mishra, S.K. et al., *Mycopathologia et Mycologia Applicata*, vol. 51 (2–3): 147–157 (1973).
Ollar, *ZBL. Bakt. HYG. 1. ABT. Orig. A 234*: 81–90 (1976).

(List continued on next page.)

*Primary Examiner*—David Redding
*Attorney, Agent, or Firm*—David V. Radack; Eckert Seamans Cherin & Mellott, LLC

[57] ABSTRACT

A method for determining the sensitivity of at least one nonparaffinophilic microorganism from a specimen obtained from a patient to different antimicrobial agent, and predetermined quantities thereof. The method includes providing at least one receptacle containing an aqueous solution and adjusting the solution to mimic the in vivo clinical conditions of said patient. The method further includes inoculating the solution with the specimen and placing into the receptacle (i) a slide coated with a carbon source and (ii) a predetermined quantity of an antimicrobial agent to be tested. By observing the nonparaffinophilic microorganism growth or lack thereof on the slide, it can be determined whether the predetermined quantity of the antimicrobial agent is effective in inhibiting growth of the nonparaffinophilic microorganism on the slide. An associated apparatus is also disclosed.

13 Claims, 1 Drawing Sheet

OTHER PUBLICATIONS

Kemper et al., *American Society for Microbiology*, 297 (Abstract) (1990).

Klatt et al., *Human Pathology*, vol. 18, No. 7: 709–714 (1987).

Bermudez et al., *The Journal of Infectious Diseases*, 165: 75–79 (1992).

Murphy et al., *American Society for Microbiology*, 277 (1983).

P. Ma et al., *Aids and Infections of Homosexual Men*, 233–234 (1989).

Havlik Jr. et al., *The Journal of Infectious Diseases*, 165: 577–580 (1992).

Inderlied et al., *Aids Clinical Review*, 165–191 (1990).

Gonzalez et al., *Diagn. Microbiol. Infect. Dis.*, 8: 69–77 (1987).

Hurley et al., *Journal of Clinical Microbiology*, pp. 1582–1587 (1989).

Kirihara et al., *Journal of Clinical Microbiology*, pp. 841–845 (1985).

Ollar et al., *Tubercle*, 71, pp. 23–28 (1990).

Kemper et al., *Annals of Internal Medicine*, 116: 466–472 (1992).

Heifets et al., *Antimicrobial Agents and Chemotherapy*, 1298–1301 (1989).

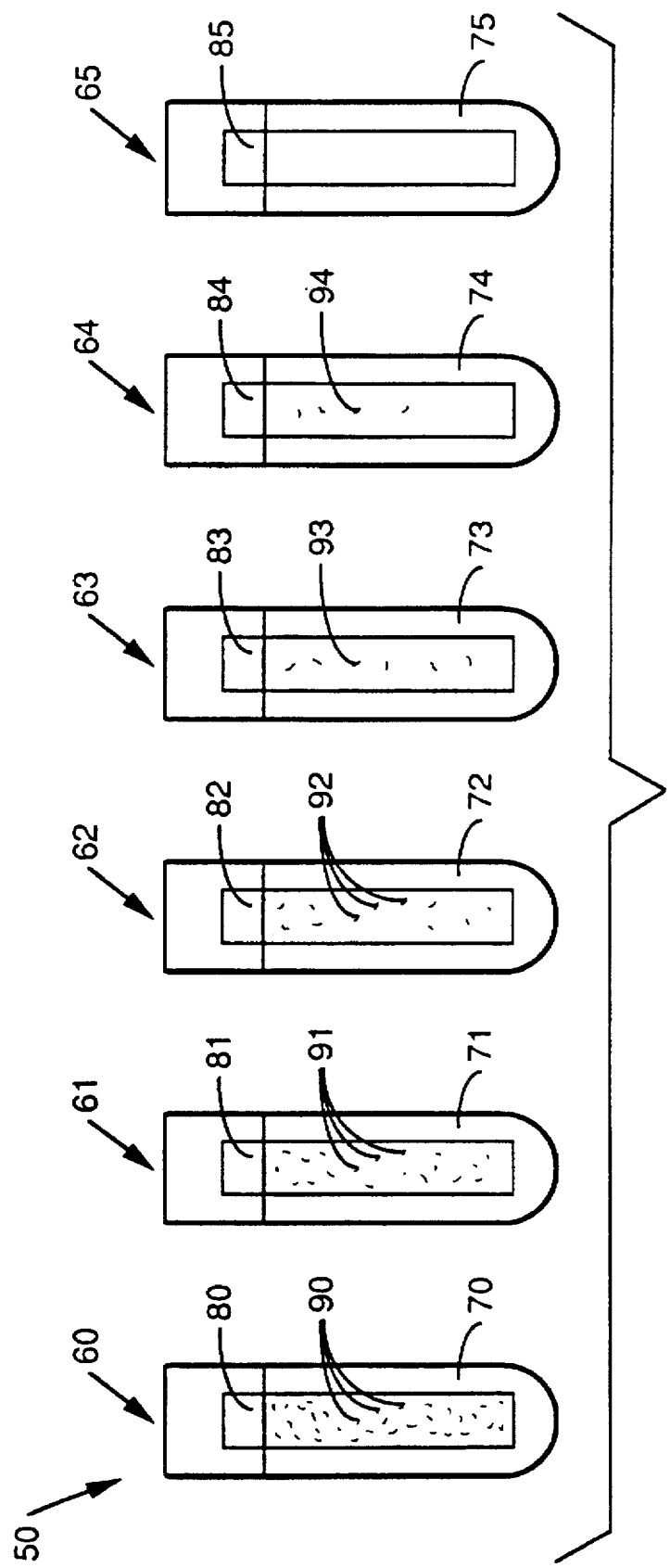

5,668,010

METHOD FOR DETERMINING THE ANTIMICROBIAL AGENT SENSITIVITY OF A NONPARAFFINOPHILIC MICROORGANISM USING VARIOUS MILIEUS AND AN ASSOCIATED APPARATUS

This is a division of application Ser. No. 08/556,033 filed Nov. 9, 1995, now U.S. Pat. No. 5,641,645.

BACKGROUND OF THE INVENTION

This invention relates to a method for determining the antimicrobial agent sensitivity of a nonparaffinophilic microorganism using various milieus and an associated apparatus.

Treating infections very often involves educated guesses by medical personnel as to the nature of the microorganism involved and the correct antimicrobial agent and quantity thereof needed to effectively treat the microorganism present in the infected tissue. Often times, there is a need to treat a mixed flora of several microorganisms. Medical personnel are acutely interested in rapidly ascertaining which antimicrobial agents, and which dosages, are necessary in order to assure effective inhibition of the growth of all microorganisms present in the patient.

In addition, certain antimicrobial agents react differently under different conditions. For example, one type of antimicrobial agent may not be effective in a low pH environment. It would thus be desirable to mimic the in vivo clinical condition of a patient in vitro in any type of antimicrobial agent sensitivity testing so that antimicrobial agent efficacy against the microorganism can be maximized.

There is presently no effective, efficient and economical way for a physician to rapidly ascertain which antimicrobial agent, and which dosage is necessary in order to treat the patient. A physician simply does not have available to him or her the type of information regarding antimicrobial agent sensitivity that would make a more exact selection of an antimicrobial agent possible and, once an appropriate antimicrobial agent is selected, facilitate a more precise dosage for treatment. If this information was available, a physician could more effectively treat the infection. Furthermore, because some antimicrobial agents are expensive, the information could be used so that only that amount of antimicrobial agent needed could be used to treat the infection. Finally, and most importantly, as antimicrobial agents can have undesired side effects, the information can be used to find the most effective antimicrobial agent and dosage thereof, which will limit the undesired side effects.

U.S. Pat. Nos. 5,153,119 and 5,316,918 disclose methods and apparatus for identifying and testing the antibiotic sensitivity of *Mycobacterium avium-intracellulare* ("MAI"), a paraffinophilic microorganism. The inventor named on those patents is Robert A. Ollar, one of the co-inventors of the invention disclosed herein. This method involves providing a receptacle containing an aqueous solution and inoculating into the solution a specimen. After this, a paraffin coated slide is placed into the receptacle. The slide is then observed for the presence or absence of growth of MAI.

Despite the existence of Dr. Ollar's patents, there still remains a need for a method of testing the antimicrobial agent sensitivity of one or more nonparaffinophilic microorganisms in a way that maximizes the efficacy of the antimicrobial agent used to inhibit growth of the one or more nonparaffinophilic microorganisms that may be present in a patient.

SUMMARY OF THE INVENTION

The invention has met or exceeded the above-mentioned need as well as others. The method for determining the sensitivity of at least one nonparaffinophilic microorganism from a specimen obtained from a patient to different antimicrobial agent and predetermined quantities thereof comprises providing at least one receptacle containing an aqueous solution and adjusting the solution to mimic the in vivo clinical conditions of the patient. The method then comprises inoculating the solution with the specimen and placing into the receptacle (i) a slide coated with a carbon source and (ii) a predetermined quantity of an antimicrobial agent to be tested. By observing the nonparaffinophilic microorganism growth or lack thereof on the slide, it can be determined whether the predetermined quantity of the antimicrobial agent is effective in inhibiting growth of the nonparaffinophilic microorganism on the slide.

An associated apparatus is also disclosed. The apparatus comprises a receptacle adapted to contain an aqueous solution, an amount of antimicrobial agent to be tested and the specimen. The apparatus further includes means for adjusting the aqueous solution to mimic the in vivo clinical conditions of the patient and a slide coated with a carbon source, the slide being adapted to being placed in the receptacle. Again, observation of the growth of the nonparaffinophilic microorganism from the specimen on the slide can be used to determine the concentration of the antimicrobial agent necessary to resist the nonparaffinophilic microorganism growth on the slide.

BRIEF DESCRIPTION OF THE DRAWING

A full understanding of the invention can be gained from the following detailed description of the invention when read in conjunction with the accompanying lone drawing which shows one embodiment of the antimicrobial agent sensitivity apparatus.

DETAILED DESCRIPTION

As used herein, the term "nonparaffinophilic microorganism" means any microorganism sustained by a carbon source other than paraffin. Examples of such nonparaffinophilic microorganisms include, but are not limited to, the following: *Helicobacter pylori; Hemophilus influenzae; Salmonella typhimurium; Mycobacterium tuberculosis; Mycobacterium paratuberculosis; Mycobacterium leprae;* Staphylococcus; Streptococcus; *E. Coli;* Listeria; Brucellae; Humemophilus; Treponema; Pneumococcus; Clostridium; Cryptococcus; Coccidioides; and Histoplasma. Also, as used herein, the term "patient" refers to a member of the animal kingdom, including human beings, whose body specimen is being processed by the method and apparatus of the invention.

The method and apparatus of the invention provide an efficient, effective and economical way of determining the sensitivity of at least one nonparaffinophilic microorganism to different antimicrobial agents and predetermined quantities thereof. Referring now to the lone FIGURE, the antimicrobial agent sensitivity method will be explained with reference to one embodiment of the antimicrobial agent sensitivity apparatus 50. The apparatus 50 consists of six receptacles in the form of test tubes 60, 61, 62, 63, 64, 65 each containing an amount of an aqueous solution 70, 71, 72, 73, 74, 75. It will be appreciated that the aqueous solution should not contain any carbon source, as it is desired to provide a sole carbon source on the slide (discussed below) in order to effectively grow the nonparaffinophilic microorganism to be tested on the slide and not in the aqueous solution. The aqueous solutions in test tubes 61–65 contain uniform intervals of increasing concentrations of an antimicrobial agent to be tested. Test tube 60 is used as a control tube that does not contain any antimicrobial agent.

In accordance with the invention, the aqueous solutions 70–75 in each of the test tubes 60–65 can be adjusted to mimic the in vivo "clinical conditions" of the patient. By "clinical conditions" it is meant at least one of the following: the pH of the in vivo milieu of the patient where the nonparaffinophilic microorganism can be found and the electrolyte levels of a patient's blood where nonparaffinophilic microorganism can be found. Adjusting the aqueous solution can be effected by numerous different methods. Adjusting the pH of the aqueous solution can be accomplished by adding hydrochloric acid (HCl) to obtain a more acidic solution or by adding sodium hydroxide (NaOH) or potassium hydroxide (KOH) in order to obtain a more basic solution. Electrolytes such as one or more selected from the group consisting of sodium, potassium, chloride, magnesium, phosphate and calcium, can be added to the solution in desired quantities in order to mimic the electrolytes in the blood of a patient from which a blood sample which may contain the microorganism is obtained.

The specimen from the patient is then inoculated into each of the test tubes 60–65. The specimen can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques.

Slides 80, 81, 82, 83, 84 and 85 coated with a carbon source are then placed into respective test tubes 60, 61, 62, 63, 64 and 65. The carbon source is a growth media for growing the nonparaffinophilic microorganisms. The slides are incubated for a period of a minimum of twenty-four (24) hours. By observing nonparaffinophilic microorganism growth 90, 91, 92, 93, 94 on the slides 80–85, the minimum inhibitory concentration ("MIC") of the antimicrobial agent necessary to prevent nonparaffinophilic microorganism growth can be determined. In this case, slide 85 has no nonparaffinophilic microorganism growth, thus the MIC concentration is found in test tube 75.

It will be appreciated that a specimen can sometimes have more than one nonparaffinophilic microorganisms present therein. For example, if a patient has a brain abscess associated with a bacterial endocarditis, the patient will most likely have a single pathogen (i.e., staphylococcus). However, there may be a mixed flora which has grown on the slide (i.e., staphylococcus and meningococci). It is imperative, however, to treat all bacterial flora, as any bacteria present are causing pathogenicity in the patient. This invention allows a physician to specify an antimicrobial agent and a particular dosage thereof which will inhibit all flora growing on the slide, and which is thus effective in treating all nonparaffinophilic microorganisms which are causing pathogenicity in the patient.

It will be appreciated that although apparatus 50 is shown with multiple receptacles and multiple slides 80–85, that the invention is not limited to multiple receptacles and multiple slides, but covers also a single receptacle and a single slide.

The carbon source and the slides 80–85 can include a gelatinous matrix containing a carbon source. A carbon source can be one or more of those selected from the group consisting of glucose, fructose, glycenol, mannitol, asparagine and casein, among others. Another embodiment can include providing a slide and coating the slide with an adhesive and securing a plurality of gel beads to the adhesive. The carbon source can then be either ionically or affinity bound to the gel beads.

The slides 80–85 with the gelatinous matrix containing a carbon source can be prepared by the following method. A receptacle, such as a laboratory beaker, is first filled with 100 ml of distilled water. Into the beaker is placed two (2) grams of agar (the gelatinous matrix) and three (3) grams of a carbon source (such as glucose). This mixture is then boiled and steam sterilized and the molten gelatinous matrix with a carbon source is poured into a petri dish, which is sitting on a hot plate. In this way the gelatinous matrix/carbon source remains molten. After this, a sterile slide such as slide 80 is dropped into the molten gelatinous matrix/carbon source and becomes coated therewith. The now coated slide is removed from the petri dish and allowed to stand for a minute or two in order to solidify the coating thereon. The slide with the coating of a gelatinous matrix containing a carbon source is then ready to be placed in one of the test tubes 60–65 containing the aqueous solution and the specimen.

An alternative method of preparing the slide involves first coating the slide with an adhesive, such as collodion and then applying a plurality of gel beads (commercially available from Pharmacia of Parsippany, N.J.) to the adhesive. The gel beads are approximately one micron in diameter. The slide containing the coating of gel beads is now immersed in a buffering agent containing the carbon source (such as glucose) to attach the carbon source to the gel beads either ionically or affinity-wise.

Nonparaffinophilic microorganisms that can be identified using the method of the invention include any microorganism sustained by a carbon source other than paraffin. Nonparaffinophilic microorganisms include, but are not limited to, *Helicobacter pylori; Hemophilus influenzae; Salmonella typhimurium; Mycobacterium tuberculosis; Mycobacterium paratuberculosis; Mycobacterium leprae;* Staphylococcus; Streptococcus; *E. Coli;* Listeria; Brucellae; Humemophilus; Treponema; Pneumococcus; Clostridium; Cryptococcus; Coccidioides; and Histoplasma.

EXAMPLE 1

A patient comes to an emergency room at a hospital complaining of abdominal pain, nausea and vomiting probably suffering from an *Helicobacter pylori* infection and possibly a *Salmonella typhimurium* infection. A gastroenterologist uses a gastrointestinal scope to obtain a specimen of the patient's stomach fluid. The scope indicates that the pH in the patient's stomach is 3.5. In the meantime, a lab technician using the apparatus of the FIGURE adjusts the pH of the aqueous solutions 70–75 by adding HCl thereto so that the aqueous solutions 70–75 have a pH of 3.5. Thus, the pH in the patient's stomach is mimicked by the pH of the aqueous solution in the apparatus shown in the FIGURE.

After this, the lab technician is instructed by the physician to add specified amounts of an antimicrobial agent to each receptacle 61–65. Receptacle 60 is a control test tube and thus does not contain any antimicrobial agent. Receptacle 65 is to contain the highest concentration of antimicrobial agent, with each successive receptacle 64–61 receiving half as much as the adjacent receptacle. In this example, the physician wants to test the sensitivity of the nonparaffinophilic microorganisms to the antimicrobial agent clarithromycin. The technician is instructed to add the following amounts to each receptacle (each receptacle contains 5 cc of aqueous solution)

| RECEPTACLE | AMOUNT |
|---|---|
| 60 | 0 |
| 61 | 0.125 mg |
| 62 | 0.25 mg |
| 63 | 0.5 mg |
| 64 | 1.0 mg |
| 65 | 2.0 mg |

After this, portions of the specimen of stomach fluid taken by the gastroenterologist from the patient are inoculated into each of the receptacles 60–65 holding a respective paraffin coated slide 80–85. After about eight days the growth or lack thereof is observed to indicate which concentration of antimicrobial agent is effective to inhibit paraffinophilic microorganism growth on the slide.

EXAMPLE 2

A patient comes to an emergency room with a cough, fever, myalgia and yellow sputum and apparently has pneumonia. The physician suspects that there is an infection caused by Hemophilus influenzae. As is standard in almost every emergency room, a chemical screen ("CSS") is performed on a blood specimen obtained from the patient. The CSS lists the electrolyte content of the patient's blood. The electrolyte content is communicated to a lab technician who in turn adjusts the aqueous solutions 70–75 in the receptacles 60–65 each holding a respective paraffin coated slide 80–85. For example, the CSS reveals that the patient has a sodium level of 120. The lab technician adjusts the sodium level of the aqueous solution (for example, distilled water) by adding sodium thereto in order to mimic the 120 level of sodium found in the patient's blood.

After this, the lab technician is instructed by the physician to add specified amounts of an antimicrobial agent to each receptacle 61–65. Receptacle 60 is a control test tube and thus does not contain any antimicrobial agent. Receptacle 65 is to contain the highest concentration of antimicrobial agent, with each successive receptacle 64–61 receiving half as much as the adjacent receptacle. In this example, the physician wants to test the sensitivity of the paraffinophilic microorganisms to the antimicrobial agent ampicillin. The technician is instructed to add the following amounts to each receptacle (each receptacle contains 5 cc of aqueous solution)

| RECEPTACLE | AMOUNT |
|---|---|
| 60 | 0 |
| 61 | 0.3125 mg |
| 62 | 0.625 mg |
| 63 | 1.25 mg |
| 64 | 2.50 mg |
| 65 | 5.00 mg |

After this, a portion of the blood specimen taken from the patient are inoculated into each receptacle 60–65 holding a respective paraffin coated slide 80–85. After about two (2) days the growth or lack thereof is observed to indicate which concentration of antimicrobial agent is effective to inhibit paraffinophilic microorganism growth on the slide.

It will be appreciated that a method for determining the antimicrobial agent sensitivity of a nonparaffinophilic microorganism is provided. The method includes adjusting the aqueous solutions used in the testing apparatus to mimic the in vivo clinical conditions of a patient from whom the specimen containing the nonparaffinophilic microorganism to be identified and tested is obtained. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method for determining the sensitivity of at least one nonparaffinophilic microorganism from a specimen obtained from a patient to different antimicrobial agents and predetermined quantities thereof, said method comprising:

a receptacle adapted to contain (i) an aqueous solution; (ii) an amount of antimicrobial agent to be tested; and (iii) said specimen;

means for adjusting said aqueous solution to mimic the in vivo clinical conditions of said patient; and a slide coated with a carbon source, said slide being adapted to being placed in said receptacle, whereby observation of the growth of said nonparaffinophilic microorganism from said specimen on said slide can be used to determine the concentration of said antimicrobial agent necessary to resist said nonparaffinophilic microorganism growth on said slide.

2. The apparatus of claim 1, wherein said adjusting means includes chemicals to adjust the pH of said aqueous solution.

3. The apparatus of claim 2, wherein said chemicals are selected from the group consisting of HCl, KOH and NaOH.

4. The apparatus of claim 1, wherein said adjusting means includes chemicals to mimic the electrolyte level in said patient's blood.

5. The apparatus of claim 4, wherein said chemicals include at least one of the group consisting of sodium, potassium, chloride, magnesium, phosphate and calcium.

6. The apparatus of claim 1, wherein said slide is coated with a gelatinous matrix containing said carbon source.

7. The apparatus of claim 1, wherein said slide is coated with a plurality of gel beads which have bound thereto said carbon source.

8. The apparatus of claim 7, wherein said carbon source is ionically bound to said gel beads.

9. The apparatus of claim 7, wherein said carbon source is affinity bound to said gel beads.

10. The apparatus of claim 7, wherein
said gel beads are adhered to said slide by an adhesive.
11. The apparatus of claim 10, wherein
said adhesive is collodion.
12. The apparatus of claim 1, wherein
said carbon source is one or more of the group consisting of glucose, fructose, glycenol, mannitol, asparagine, urea, casein and hydrolyzate.

13. The apparatus of claim 1, including
a plurality of receptacles each adapted to contain (i) an aqueous solution; (ii) an amount of antimicrobial agent to be tested; and (iii) said specimen; and
a plurality of slides each coated with a carbon source, each of which is adapted to being placed in one of said receptacles.

* * * * *

UNITED STATES PATENT AND TRADEMARK OFFICE
CERTIFICATE OF CORRECTION

PATENT NO. : 5,668,010

DATED : September 16, 1997

INVENTOR(S) : Mitchell S. Felder and Robert-A. Ollar

It is certified that error appears in the above-identified patent and that said Letters Patent is hereby corrected as shown below:

Column 1, line 54, "Robert A." should be --Robert-A.--.

CLAIM 1, column 6, line 26, "A method" should be --An apparatus--.

CLAIM 1, column 6, line 29, ", said method" should be deleted.

Signed and Sealed this

Eleventh Day of August 1998

Attest:

BRUCE LEHMAN

Attesting Officer

Commissioner of Patents and Trademarks